US007166257B2

(12) United States Patent
DeSilets et al.

(10) Patent No.: US 7,166,257 B2
(45) Date of Patent: *Jan. 23, 2007

(54) MULTIWELL TEST APPARATUS

(75) Inventors: Kenneth DeSilets, Westford, MA (US); Jeanne Phillips, Littleton, MA (US); Donald B. Rising, Stow, MA (US)

(73) Assignee: Millipore Corporation, Billerica, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/783,003

(22) Filed: Mar. 17, 2005

(65) Prior Publication Data

US 2005/0163666 A1    Jul. 28, 2005

(51) Int. Cl.
*B01L 11/00* (2006.01)
(52) U.S. Cl. .................... 422/101; 422/99; 422/100; 422/102; 435/285.1; 436/180
(58) Field of Classification Search .......... 422/99–102; 436/180; 435/305.2, 285.1; 210/406
See application file for complete search history.

(56) References Cited

U.S. PATENT DOCUMENTS

| 4,927,604 | A | * | 5/1990 | Mathus et al. ............... 422/101 |
| 4,948,564 | A | * | 8/1990 | Root et al. .................. 422/101 |
| 5,141,718 | A | | 8/1992 | Clark |
| 5,265,754 | A | | 11/1993 | Dalbo |
| 5,462,874 | A | | 10/1995 | Wolf et al. |
| 5,650,323 | A | | 7/1997 | Root |
| 5,707,869 | A | | 1/1998 | Wolf et al. .................. 435/401 |
| 5,801,055 | A | | 9/1998 | Henderson |
| 5,837,198 | A | | 11/1998 | Itani |
| 5,972,694 | A | * | 10/1999 | Mathus .................... 435/288.4 |
| 6,159,368 | A | | 12/2000 | Moring et al. |
| 2002/0189374 | A1 | * | 12/2002 | DeSilets et al. ......... 73/864.51 |

FOREIGN PATENT DOCUMENTS

EP    0 596 482    5/1994

(Continued)

OTHER PUBLICATIONS

International Search Report.

(Continued)

*Primary Examiner*—Jill Warden
*Assistant Examiner*—Jyoti Nagpaul
(74) *Attorney, Agent, or Firm*—Millipore Corporation (57) ABSTRACT

A multiwell test apparatus formed of a multiwell filter plate having a plurality of wells and a first feeding plate and a second receiver plate is provided. The wells of the multiwell filter plate each have an open bottom surface to which a membrane is attached, at least one first access hole providing access to the feeding/receiver plate below, a pair of alignment pins designed to fit alignment holes in the feeding/receiver plates in a particular arrangement. The first feeding plate is a single well plate or a multiwell plate used solely for feeding. The second receiver plate is a multiwell plate having the same number of wells as the filter plate and aligned so as to receive the wells of the filter plate therein used as the assaying plate. The use of alignment holes in the feeding/receiver plates and alignment posts in the filter plate ensure precise alignment of the plates when together.

5 Claims, 11 Drawing Sheets

FOREIGN PATENT DOCUMENTS

| | | | |
|---|---|---|---|
| EP | 0 747 476 | | 12/1996 |
| FR | 2548685 | * | 7/1983 |
| WO | WO 98/35013 | | 8/1998 |
| WO | WO 99/21958 | | 5/1999 |

OTHER PUBLICATIONS

"Selection of Invasive and Metastatic Subpopulations from a Heterogeneous Human Melanoma Cell Line", BioTechniques, Vo. 9, No. 3 (1990), p. 324.

1. Photograph of top plate of MultiScreen Dual Access plate prototype, publicly provided by Millipore Corporation in Feb. 1993.

2. Photograph of three piece MultiScreen Dual Access Cell Culture System prototype, publicly provided by Millipore Corporaiton in Feb. 1993.

European Search Report dated Nov. 15, 2004, 3 pages.

* cited by examiner

MULTIWELL TEST APPARATUS

BACKGROUND OF THE INVENTION

This invention relates to a multiwell test apparatus which is utilized for promoting fluid interactions such as by growing cells in a nutrient medium within the wells. More particularly, this invention relates to such a multiwell filter plate of a multiwell test apparatus which permits adding or removing liquid from the feeding plate of a multiwell test apparatus without disturbing a material such as cells within the wells and two plates, one for growing the cells and the other for the assaying of the cells.

At the present time, multiwell test apparatus for testing samples include a multiwell filter plate, a single well feeding plate, a multiwell receiver plate and a lid. The wells of the multiwell filter plate are formed of a tubular member with an open end to which is attached a membrane such as a microporous membrane. The tubular members can be inserted into a single well feeding plate containing a nutrient medium so that cells in the wells can be attached to the membrane and grown thereon. The cells are fed as nutrients pass from the nutrient medium through the membrane and to the cells at a rate controlled by the concentration gradient of nutrients from the medium to the cells. The nutrient medium in the feed tray is periodically replenished to maintain cell growth. It is desirable to effect replenishment of the nutrient medium quickly and in a manner which avoids damage to the membranes and the cells.

After the desired level of cell growth on the membranes of the wells has been attained, the multiwell filter plate can be utilized in conventional assay methods. These assay methods generally are effected by positioning the membranes and cells on the multiwell filter plate into the wells of the multiwell receiver plate positioned below the multiwell filter plate having the same number of wells in register with the wells of the filter plate. The wells of the multiwell receiver plate contain a liquid composition to be assayed. The composition to be assayed diffuses into the cells and then through the membrane. The resultant liquid products within the wells of the multiwell filter plate or in the wells of the multiwell receiver plate then are assayed to determine the capability of the composition being assayed to permeate the cell barrier.

An important component in the drug discovery and development process is the determination of the oral absorption and bioavailability of new compounds. In order to perform this evaluation in a cost effective, high throughput and sensitive assay, it is ideal to use an in vitro device with a multitude of wells, containing cells and a small amount of assay material and automation. Classically, the determination of in vitro oral absorption characteristics is performed using a defined epithelium cell line and measuring the apparent transport rate of the drug across a monolayer of the cells. More recently it is possible to rank/order the passive transport rate of potential drug candidates using an artificial membrane barrier. The values generated from these in vitro experiments are valuable methods for screening the most likely successful drug candidates long before the oral absorption rate are validated by in vivo measurements. A typical experiment for determining the drug absorption characteristics of a known or unknown chemical compound is performed as follows. The multiwell device is seeded with epithelium cells on top of the filter in a defined medium. The same medium is also added to the single well feeding plate, located below and in fluid contact with the device containing the cells. The cells are allowed to proliferate and differentiate over a number of days. The nutrient medium is periodically replaced with fresh medium to replenish exhausted nutrients and remove waste and dead cells. At the end of a growing time, the cells and multiwell device are gently washed with an isotonic buffer to remove protein and residual nutrient medium. At this time, the multiwell filter plate is transferred to the multiwell receiver plate and the chemicals to be assayed are introduced to either the compartment above the cell layer or below the cells and filter support in the multiwell receiver tray. The opposing chamber is filled with drug free buffer and the multiwell device is incubated for some period of time, typically at 37 degrees Centigrade with shaking. Samples then are removed from either compartment for assay. If multiple time points are desired, multiple time-spaced samples are taken from either compartment, and buffer is added to the compartment to replace the sample volume. It is important that the membrane or cell layer not be disturbed during sample removal or buffer addition. The amount of drug/chemical that is transported across the cell barrier can be determined by a variety of analytical methods, but typically is determined using LC-MS/MS (Liquid Chromatography-Mass Spectrometry-Mass Spectrometry).

After the cells have been satisfactorily grown and the single well feeding plate is to be replaced by the multiwell receiver plate, it is desirable to minimize transport of the nutrient medium to the multiwell receiver plate thereby to minimize dilution of the composition being assayed. Thus, it is desirable to remove any droplets of nutrient medium retained on the lower surfaces of the membranes after the multiwell filter plate is removed from the nutrient medium in the single well feeding plate.

Also, it would be desirable to provide a multiwell filter plate of a multiwell test apparatus which facilitates liquid addition or removal from the wells of the multiwell filter plate in a manner which preserves the integrity of the membranes and when present, cells on the membrane. In addition, it would be desirable to provide such a multiwell filter plate which can be utilized in conjunction with a multiwell receiver plate subsequent for use in conjunction with the single well feeding plate.

Also it would be desirable to provide a multiwell test apparatus with a feed plate that has various means for the provision or removal of liquids in the feed plate without disturbing the cells and which minimizes the sloshing of the liquid in the feed tray during handling.

SUMMARY OF THE INVENTION

This invention will be described herein with reference to the growing and use of cells on a membrane positioned and secured to the bottom of each of a multiplicity of wells. However, it is to be understood that the present invention need not be used in conjunction with cells. Other representative uses include filtration, dialysis or the like.

The present invention provides a multiwell test apparatus comprised of a multiwell filter plate having a multiplicity of wells each including a membrane for retaining a sample, such as cells, on the membrane and two plates for use in conjunction with the growing of the cells and the assaying of the cells. The multiwell filter plate is first used in conjunction with a feeding plate that may be either a single or multiwell device, in a step wherein cell growth is promoted and then is used in conjunction with a multiwell receiver plate wherein sample testing is effected. The single well feeding plate promotes quick replenishment of the nutrient medium while avoiding damage to the permeable barrier, such as membranes, secured to a multiplicity of wells or damage to cells positioned on the membranes. The single well feeding plate can include a flat or an inclined bottom surface for the nutrient medium surrounded by walls which retain the nutrient medium on the bottom surface. The bottom surface can preferably be inclined so that the nutrient medium can be supplied through the multiwell filter plate to the single well feeding plate at a high point of the inclined bottom surface and so that the nutrient medium can be removed through the multiwell filter plate from the bottom surface of the single well feeding plate at a low point of the inclined bottom surface. The multiwell feeding plate allows for the use of less volume of nutrients overall, the potential to use different medias in different wells if desired, isolates each well to prevent contamination of one well from spreading to another well and reduces the potential for slippage of the media when the apparatus is moved.

The multiwell filter plate of this invention is provided with an input access hole through which the nutrient medium is supplied to the single well feeding plate and preferably a separate drainage access hole through which the nutrient medium is removed from the single well feeding plate. The access hole(s) permit insertion of a liquid handling device such as a syringe, cannula, pipette or the like therethrough for introduction or drainage of the nutrient medium while avoiding the need for separating the multiwell filter plate from the single well feeding plate in order to replenish or supply nutrient medium to the single well feeding plate.

The wells of the multiwell filter plate may be shaped to form at least one shelf extending from a wall of the well and spaced apart from the membrane so that the shelf provides a support surface for an end of the liquid handling device such as a syringe, cannula, pipette or the like to prevent its contact with the permeable barrier, typically a membrane, and the growing cells. Additionally, the shelf serves as a deflector when media is injected into the well. The shelf allows the media to be added without disturbing the growing cells.

The multiwell filter plate of this invention is used in a second step in conjunction with a multiwell receiver plate, the wells of which house a liquid that interacts with the membrane or cells within the wells of the multiwell filter tray. An access hole is positioned adjacent each well of the multiwell filter tray to provide direct access to the wells of the multiwell receiver plate positioned below the multiwell filter plate.

The single well feeding plate may have posts, protrusions and/or baffles to allow for the removal of liquid droplets from the bottom of the wells of the multiwell filter plate and to control the sloshing of the liquid when the filter plate/single well feeding plate combination are handled.

Alignment guides are also used between the filter plate and each of the bottom plates to ensure that the wells of the filter plate are arranged in a particular order regardless of whether it is used with single or multiwell bottom plate.

The use of posts or protrusions to allow for the removal of pendant droplets on the bottom of the wells of the filter plate as it removed from a single well feeding plate may also be included.

The use of one of more baffles to reduce the movement of the liquid in the single well feeding plate during handling may also be included.

DESCRIPTION OF SPECIFIC EMBODIMENTS

While the present invention is described with reference to effecting cell growth and transport studies in a multiplicity of wells, it is to be understood that the present invention is applicable to manipulations involving access areas for introducing or removing a liquid to effect the desired processing, for example dialysis or diffusional separation while avoiding movement of materials on the membranes in the wells.

Figure 1:
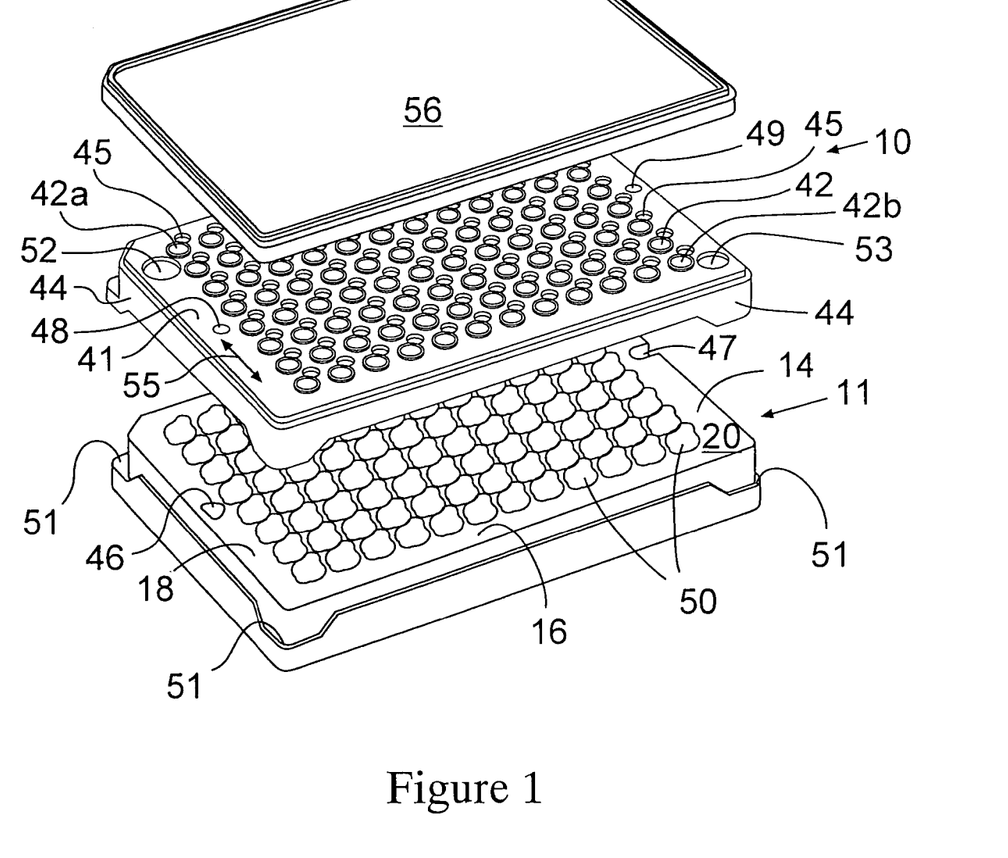
FIG. 1 is a top exploded view of a multiwell test apparatus utilizing the multiwell filter plate of this invention.
Figure 2:
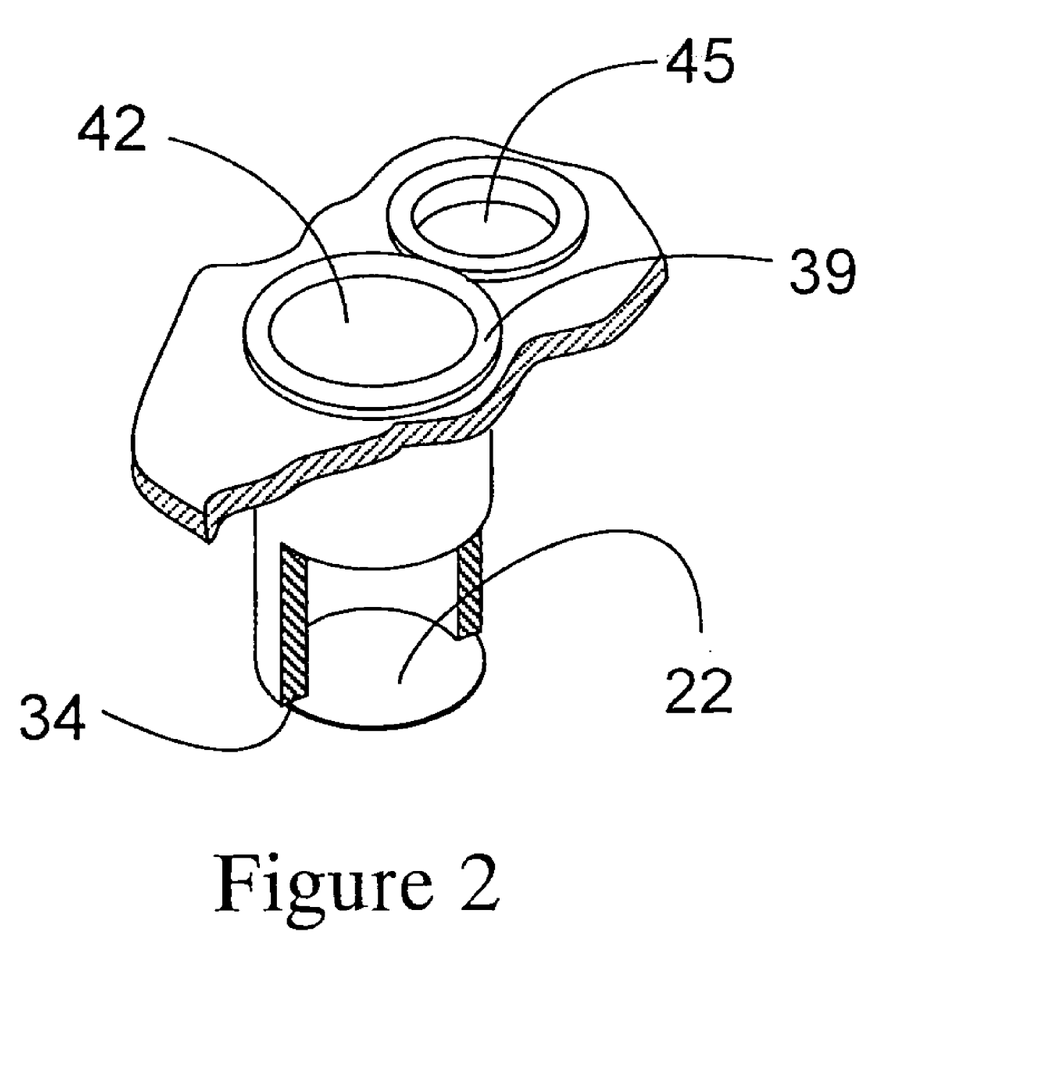
FIG. 2 is a partial cross-sectional view of a multiwell filter plate of this invention.

Referring to FIG. 1 the multiwell filter plate 10 of this invention comprises a plate 41 including a plurality of wells 42, each of which is paired with an access hole 45. As shown in FIG. 2, each well 42 comprises a hollow member 39 having a lower opening 34 to which is secured a permeable barrier 22 such as a microporous membrane. By permeable barrier, it is meant that the barrier is permeable to liquids and gases but not particulate materials over the rated pore size of the barrier. Membranes, especially microporous membranes, are a preferred material for the barrier, although other materials such as ultrafiltration membranes, glass mats or fabrics, or woven or non-woven plastic materials may be used. The member 39 is hollow and may be formed in a variety of shapes. Tubular designs are preferred and the industry standard for such wells, although wells of other shapes such as triangular, rectangular, square or hexagonal may be used. Access hole 45 is shown as being adjacent to the each associated well 42.

Figure 5:
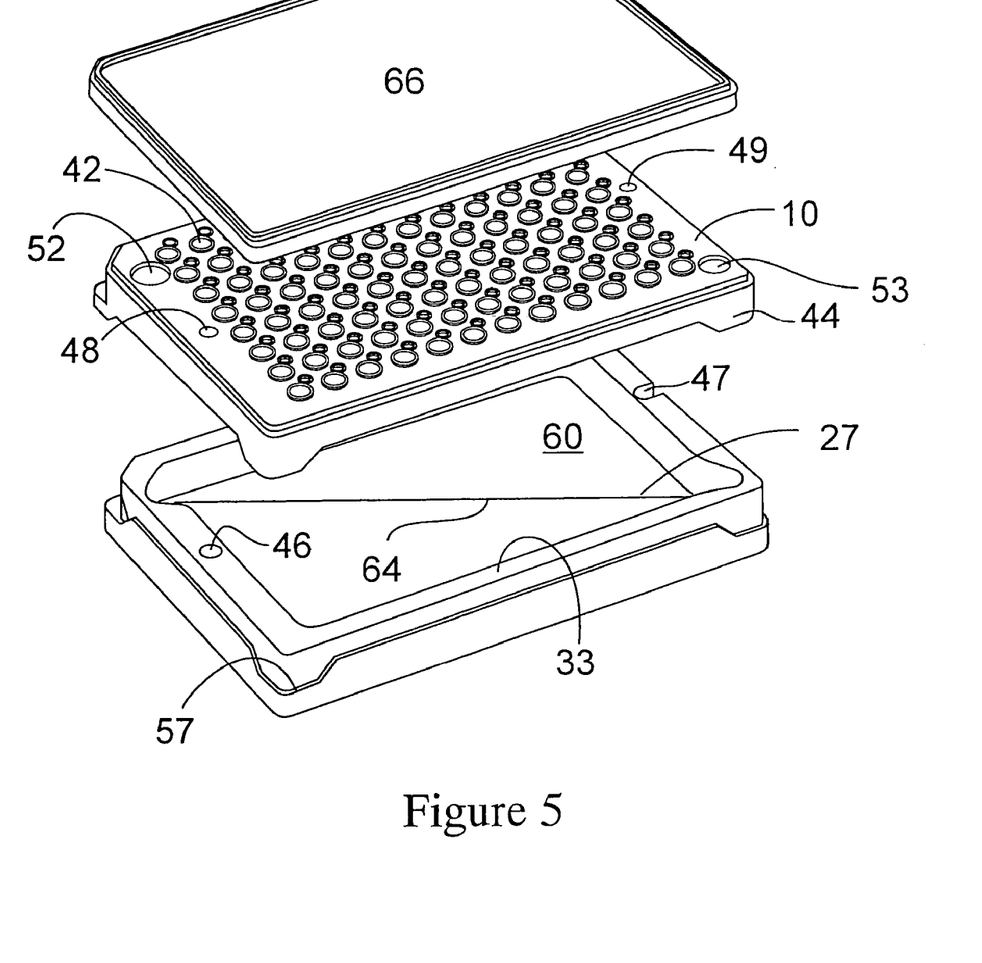
FIG. 5 is a perspective view of a single well feeding plate which can be utilized with the multiwell filter plate of this invention.

Access holes 53 and 52 provide access to single well feeding plate 33 (FIG. 5) into which liquid or gel nutrient medium is introduced and removed. One or more access holes may be used to perform this function. As shown two are used, although one or more than two (e.g. four, one in each corner) may also be used. The single well feeding plate is preferably used solely for feeding purposes in this invention. Nutrient medium can be removed and introduced through access holes 53 and 52 with a conventional liquid handling device, such as a syringe, extending through access holes 53 and 52. While two access holes 52, 53 are shown; one could use a single access hole if desired. As shown, the single well plate has an inclined bottom 64 with the drainage area 27 positioned at the lowest point of surface 60, so that complete drainage can be easily effected. Alternatively, drainage and replenishment can be effected simultaneously without the need to move multiwell filter plate 10 relative to single well feeding plate 33 (FIG. 5). In another embodiment of the single well feeding plate (not shown), the use of a flat bottomed plate may be utilized.

In the embodiment shown in FIG. 1, multiwell filter plate 10 is provided with posts 48 and 49 which fit respectively in holes 46 and 47 of multiwell receiver plate 11 when multiwell receiver plate 11 is positioned below multiwell filter plate 10. Alternatively, posts 48 and 49 can be positioned within holes 71 and 73 of single well feeding plate 33 (FIG. 5) when single well feeding plate 33 is positioned below multiwell filter plate 10. Posts 48 and 49 are positioned a distance away from each other in the direction of arrow 55 (e.g. asymmetrically opposed) so that well 42*a* is always in the upper left hand position while well 42*b* is always in the lower right hand position shown in FIG. 1. By so positioning wells 42*a* and 42*b*, all the wells 42 in multiwell filter plate 10 can be identified by their position. Optional removable lid 56 is utilized to provide sterility to the wells 42 and to minimize evaporation of nutrient medium.

Figure 3:
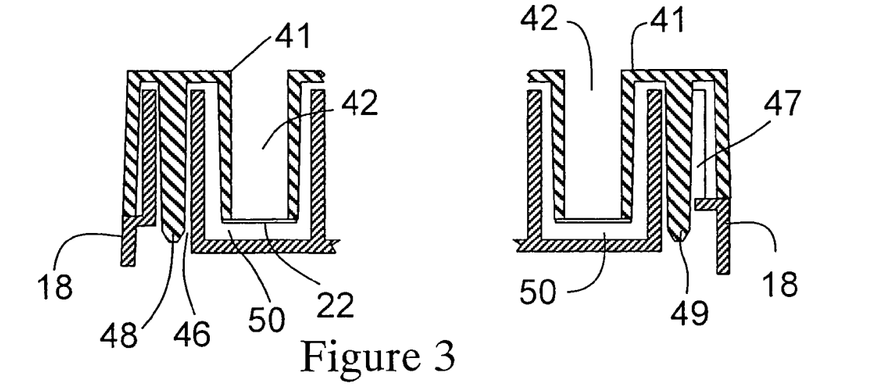
FIG. 3 is a partial cross-sectional view of the multiwell filter plate and multiwell feeding or receiver plate of this invention.
Figure 3A:
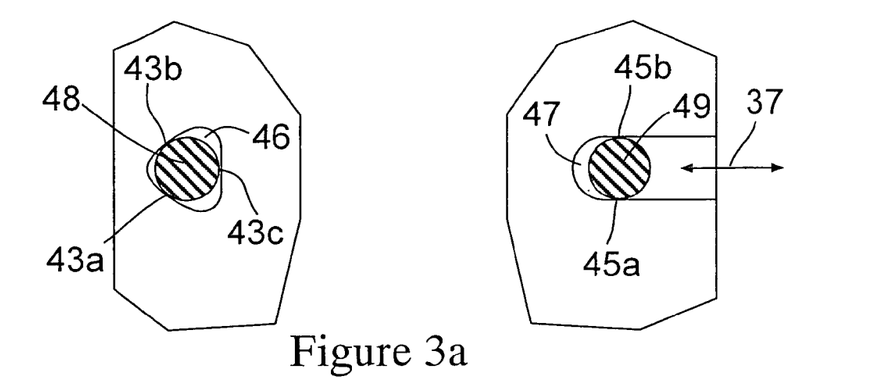
FIG. 3A is a partial perspective view of the pins/holes alignment of the present invention.
Figure 4:
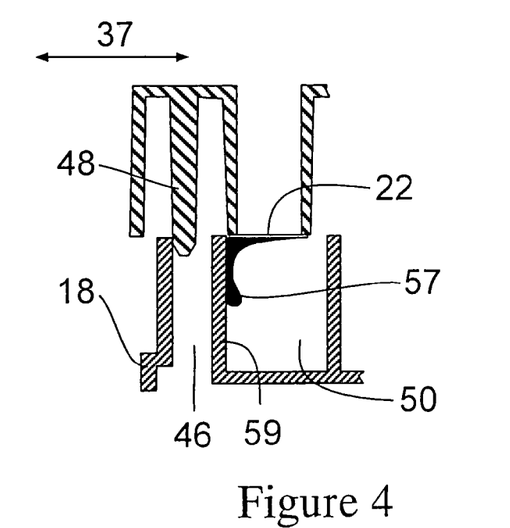
FIG. 4 is a partial cross-sectional view of a multiwell filter plate and multiwell feeding or receiver plate of this invention.

Referring to FIGS. 3 and 3*a*, the posts 48 and 49 fit respectively into holes 46 and 47. Hole 46 is shaped with a three-sided perimeter so that post 48 contacts the walls of the hole 46 at three points 43*a,b* and *c*. This mode of contact prevents multiwell filter plate 10 from moving laterally with respect to the multiwell receiver plate 11. Post 49 contacts the walls of hole 47, in this embodiment shown in the form of a slot, at two points 45*a* and *b* so that part to part variations, or misalignment can only be accommodated in the direction shown by arrow 37. The lowermost ends of posts 48 and 49 are beveled to promote ease of insertion of the posts 48 and 49 into holes 46 and 47. In addition, as shown in FIG. 3, since the tip of post 48 is smaller than hole 46, and post 48 is longer than well 42 and since the tip of post 49 is smaller than hole 47 and post 49 is longer than well 42, this permits the multiwell filter plate 10 to move laterally as exemplified by arrow 37 when it is partially lifted from the multiwell receiver plate 11 as shown in FIG. 4. This lateral movement is not limited to the direction or arrow 37 if the posts 48 and 49 taper uniformly as shown. This lateral movement permits contact of droplet 57 onto inner wall 59 of well 50 of the receiver plate 11 so that droplet 57 moves into well 50 from the membrane 22. This touch off of the droplet 57 prevents cross-talk contamination of the liquid into an adjacent well to the well 50 shown.

It is to be understood that the posts 48 and 49 can be the same length or shorter than the wells 42 so long as they are longer than holes 46 and 47. Controlled lateral movement of the multiwell filter plate 10 is effected by shaping the posts 48 and 49 and the holes 46 and 47 so that when the posts 48 and 49 are partially removed from holes 46 and 47 a space is formed between the posts 48 and 49 and the interior walls of holes 46 and 47 which permits lateral movement of the posts 48 and 49 within the holes 46 and 47 and, thus the lateral movement of the multiwell filter plate 10 so that touch off of the droplets 57 is effected. This can be effected, for example, by forming inclined surfaces on the posts 48 and 49 from the top of the posts to the bottom of the posts where the walls of the holes 46 and 47 are vertical.

An additional advantage of using the alignment pins to align the top and bottom plate of the device is that the alignment is precise and consistent and it does not require a precise fit between the sides of the plates. In this way there can be some sloppiness or forgiveness in the tolerances of the fit between the plate sides but one is guaranteed accurate alignment of the plates due to the pin/hole arrangement. This is of particular advantage in robotic applications as the plates can be easily manipulated by the robotic handler without too much regard being given to the required fit between the respective sides. Moreover, it allows one to design a plate system that allows the robotic handlers to slightly squeeze the plates and yet still get easy and complete separation from each other and exact and consistent alignment.

The use of multiwell filter plate 10 is exemplified with reference to FIG. 1. As shown in FIG. 1, the multiwell filter plate 10 is positioned above multiwell receiver plate 11 which includes a multiplicity of wells 50, such as 96 wells that correspond in number and size and location to those of the filter plate 10. The multiwell receiver plate 11 may be used as a feeding tray in lieu of the single well feeding tray or it may be used in testing such as in drug assay studies of cells grown in the wells of the filter plate 10. An advantage to using a first multiwell receiving plate as a feeding tray is that the volume of fluid required is less than that of a single well tray which minimizes feeding costs. It also has the advantage of isolating each well from the other such as during cell growth so that if one well becomes contaminated or non-functional, the other wells survive for further testing. Lastly, the use of a multiple well receiving tray as a feeding tray reduces the potential for spillage over that of a single or small number of wells tray (e.g. 2–4 wells). This may be of advantage in robotic handling applications. In use, the multiwell receiver plate 11 is positioned such that a membrane 22 (FIG. 2) of the wells 42 extends into only one well 50 of the multiwell receiver plate 11. Each of the wells 42 has associated therewith an access hole 45 which permits access to a well 50 of the multiwell receiver plate 11 utilized during a sample assay step. The multiwell filter plate 10 can be provided with four legs 44 which fit into recesses 51 of multiwell receiver plate 11 thereby to provide mechanical stability of multiwell filter plate 10. The legs 44 also serve to position the membranes 22 to avoid contact with the bottom surfaces of the wells 50 thereby to promote contact of liquid with the membranes 22. In addition, the legs 44 provide protection of the membrane 22 if the multiwell filter plate 10 is placed on a bench top. The device is used similarly with the single well feeding plate of FIG. 5. However as there is one common well in the single well feeding plate, the liquid in the plate is shared between the wells of the filter plate. The legs 44 and recesses 51 still prevent contact between the bottom of the feeding plate and the membranes.

Figure 6:
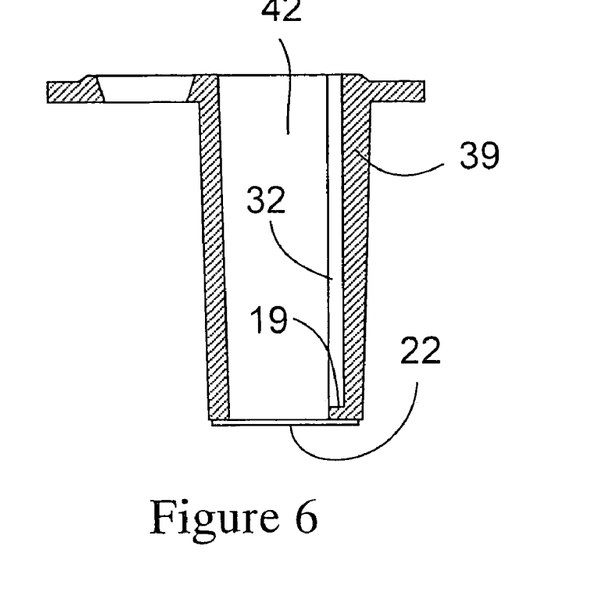
FIG. 6 is a partial cross-sectional view of an alternative well design for a multiwell filter plate of this invention.

Referring to FIG. 6, the well may have at least one recess 32 formed in its sidewall 39 with a shelf 19 formed at the bottom of the recess 32 adjacent membrane 22. The recess 32 and shelf 19 may be formed by conventional molding.

Figure 6A:
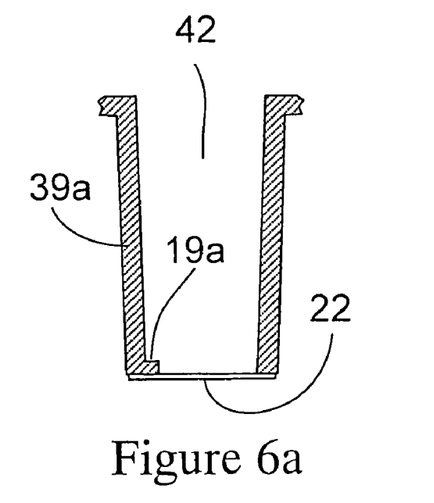
FIG. 6a is a partial cross-sectional view of an alternative well design for a multiwell filter plate of this invention.

Referring to FIG. 6*a*, the tubular member 39*a* of the well 42 of the filter plate may optionally be used to form a shelf 19*a*. The shelf 19*a* is formed by conventional molding, such as injection molding or overmolding wherein the shelf 19*a* extends from tubular member 39*a* adjacent membrane 22.

Figure 6B:
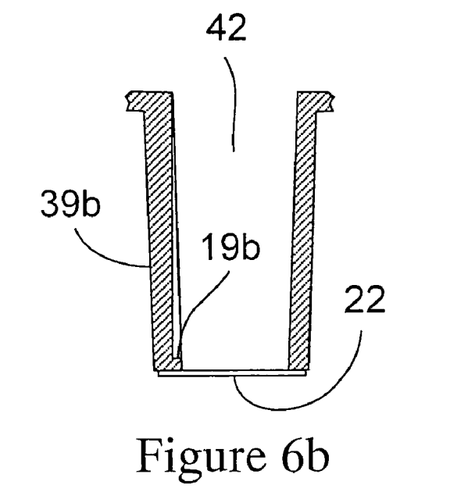
FIG. 6b is a partial cross-sectional view of an alternative well design for a multiwell filter plate of this invention.

Referring to FIG. 6b, the shelf 19b is formed by conventional molding, such as injection molding or overmolding, wherein a portion of wall 39b is recessed.

Figure 7:
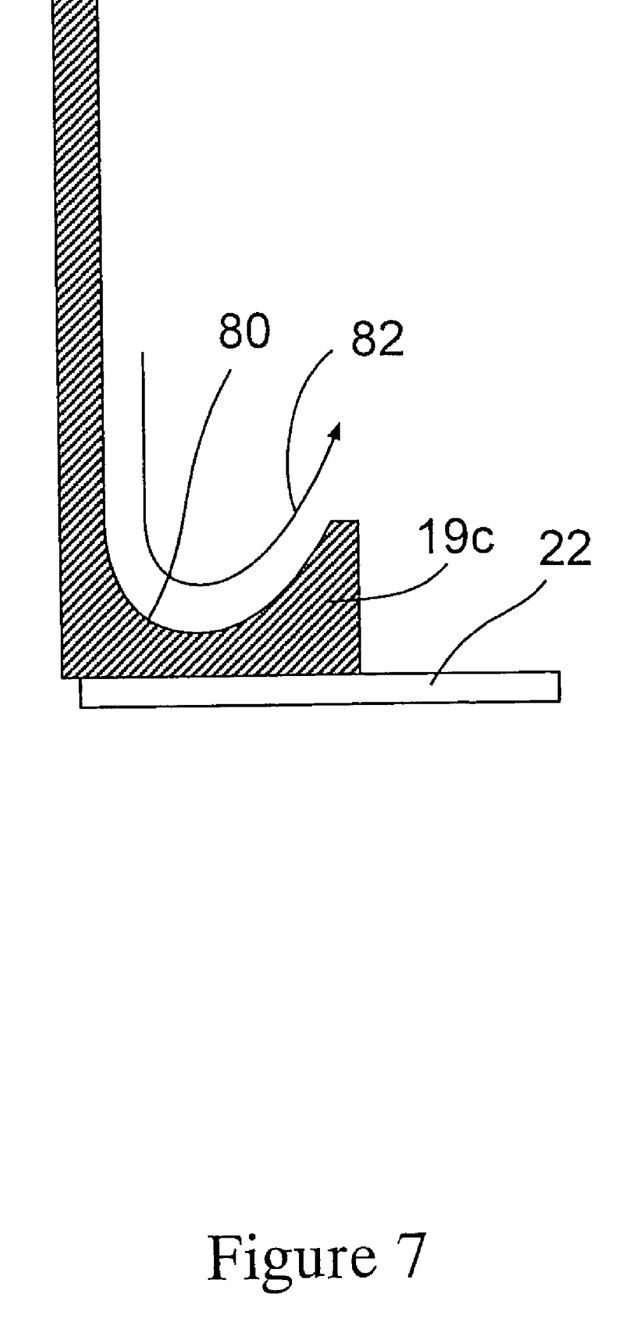
FIG. 7 is a cross-sectional view of an alternative well construction of this invention.

As shown in FIG. 7, the shelf 19c can include a concave surface 80 which serves to direct liquid from a syringe, cannula, pipette and the like in the direction shown by arrow 82. This serves to reduce the pressure of the liquid from the syringe on membrane 22 thereby preserving the integrity of the membrane 22 and preserving the integrity of a cell layer on membrane 22.

Figure 8:
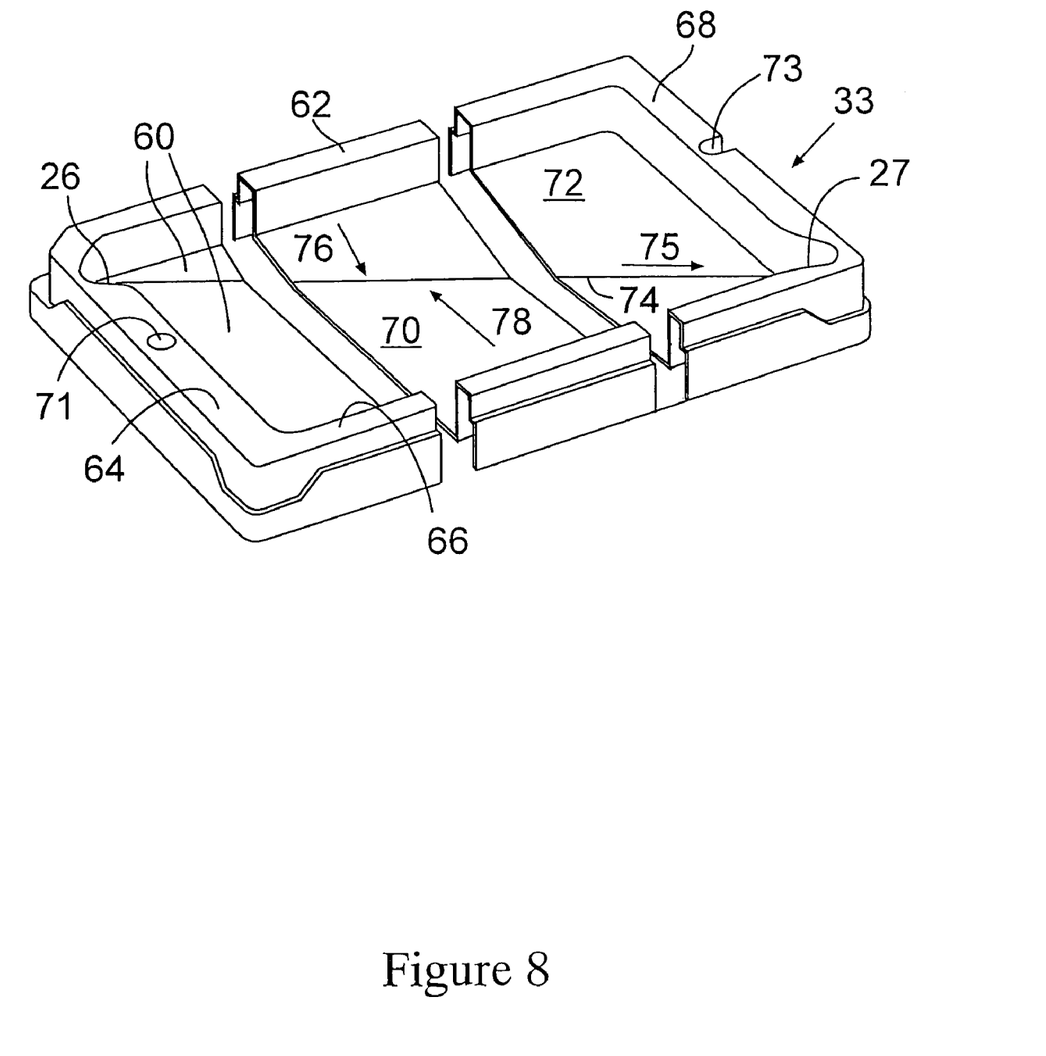
FIG. 8 is a perspective view of an alternative embodiment of the single well feeding plate of the present invention.

Referring to FIG. 8, the single well feeding plate 33 having hole 71 and slot 73 and utilized with the multiwell filter plate of this invention includes walls 62, 64, 66 and 68 and support surface 60 to house a nutrient medium. The support surface 60 includes two surface subsections 70 and 72 separated by drain path 74. The surface subsections 70 and 72 are inclined downwardly from walls 66 and 62 in the direction exemplified by arrows 78 and 76 toward drain path 74. Drain path 74 provides fluid flow from liquid introduction area 26 on surface 60 to liquid drain area 27 as exemplified by arrow 75.

Figure 9:
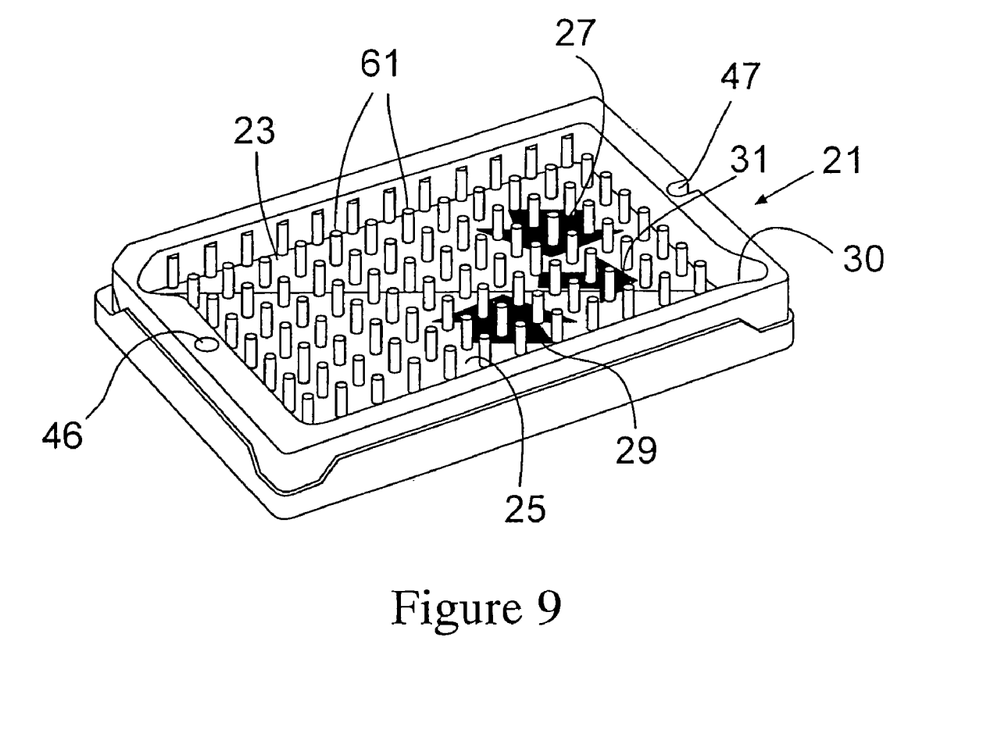
FIG. 9 is a perspective view of an alternative embodiment of the single well feeding plate of the present invention.

Referring to FIG. 9, an alternative single well feeding plate 21 utilized with the multiwell filter plate of this invention is illustrated. This embodiment is provided with one or more protrusions extending from the inner and supporting surface of the single well feeding plate a distance which permits their contact with the membranes of the wells of the multiwell filter plate. As shown, the protrusions are posts 61 extend from surfaces 23 and 25 to a position where they can contact the membrane 22 of wells 42. The purpose of this contact is to effect drainage of excess liquid from the bottom surface of the membrane 22 to the posts 61 and into the single well feeding plate 21. This practice is commonly called "touch-off" in the field of pipetting and means to remove residual liquids/sample adhering to pipette tips. The shape of the protrusions may be varied so long as they provide the same function. Typical shapes include conical, pyramidal, rectangular and dimpled. A post 61 is positioned adjacent each well 42. The single well feeding plate 21 also comprises inclined surfaces 23 and 25 which effect liquid flow in the directions of arrows 27 and 29 and in the direction of arrow 31 into the drainage area 30. Movement of multiwell filter plate 10 toward posts 61 can be effected by any conventional means.

Figure 10:
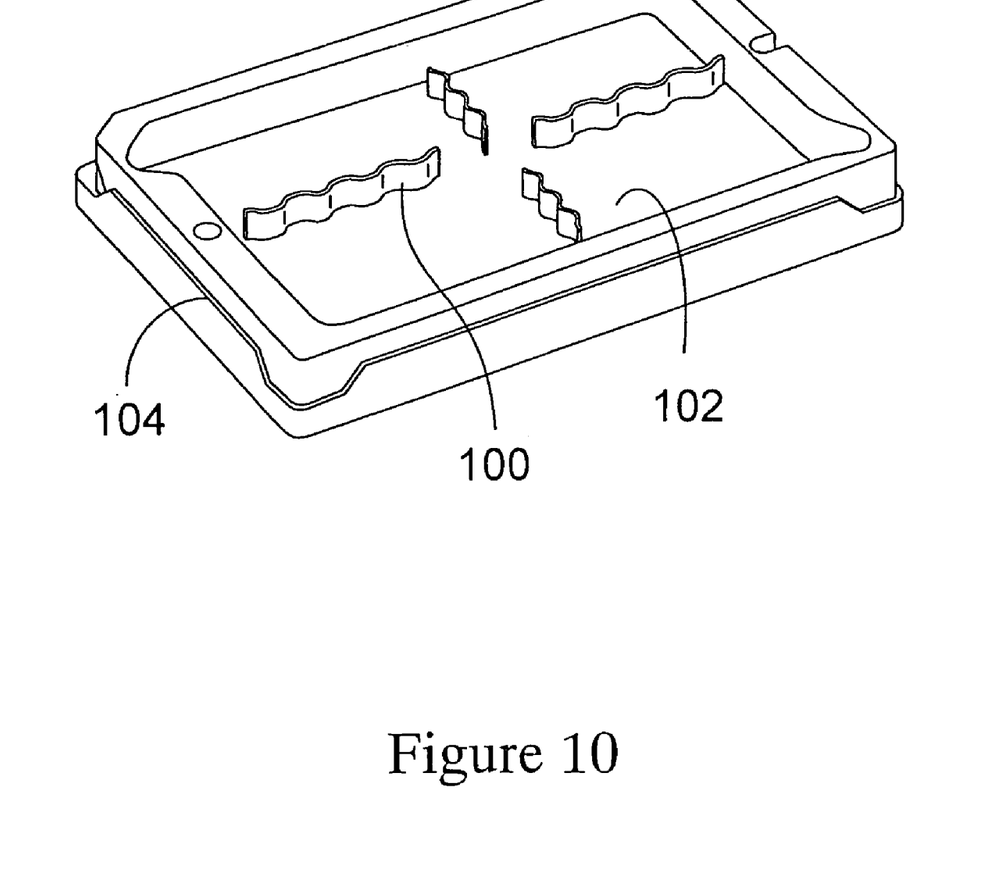
FIG. 10 is a perspective view of an alternative embodiment of the single well feeding plate of the present invention.

In a further alternative embodiment of the present invention, one may use one or more baffles to reduce the movement or sloshing of the liquid in the feed tray, especially during handling, by humans or robotic equipment. FIG. 10 shows one such embodiment.

In this embodiment, the use of four baffles 100 is shown. The baffles 100 are attached to the bottom 102 of the feed tray 104. Preferably they are formed as part of the feed tray 104 such as by injection molding along with the tray when it is made although they may added as a separate element that is either attached to the tray sides or bottom or allowed to rest freely on the bottom of the tray. As shown, the baffles are arranged in a cross-like pattern and are separate and distinct from each other. As shown, they are also each formed in a repetitive "S" or wavy pattern. Alternatively, the baffle(s) 100 may be straight or curvilinear or crossed (X-like elements) or the like so long as they are able to perform their function while allowing the cell tray (not shown) to fit into the feed tray 104 and to allow the fluid in the feed tray 104 to flow so that no dead spots occur. As shown, the baffle(s) 100 do not touch the sidewalls of the tray 104. They may if desired. Preferably when they do touch the sidewalls, there are one or more through holes formed in the baffle, preferably along its lower edge to allow for unimpeded fluid movement along the walls.

The height of the one or more baffles 100 is not critical so long as it is sufficient to help reduce the amount of movement of the liquid in the feed tray 104 while being handled. Typically, one can have the baffle height between 20% and 100% of the depth of the liquid in the tray 104. In another embodiment the baffle(s) height is between 35% and 80% of the depth of the liquid in the tray 104. Alternatively, the baffle(s) height is between 50% and 75% of the depth of the liquid in the tray 104.

The number of baffles is not critical. In one embodiment, it is preferred that only one baffle, either running at least partially the length or the width of the tray be used. In another embodiment, it is preferred that at least two baffles, at some defined cross direction to each other, be used. In such an embodiment, the two baffle(s) may be from about 25 degrees to 90 degrees to the direction of the other so as to ensure that the liquid movement is controlled in both the tray length and tray width directions.

Figure 11A:
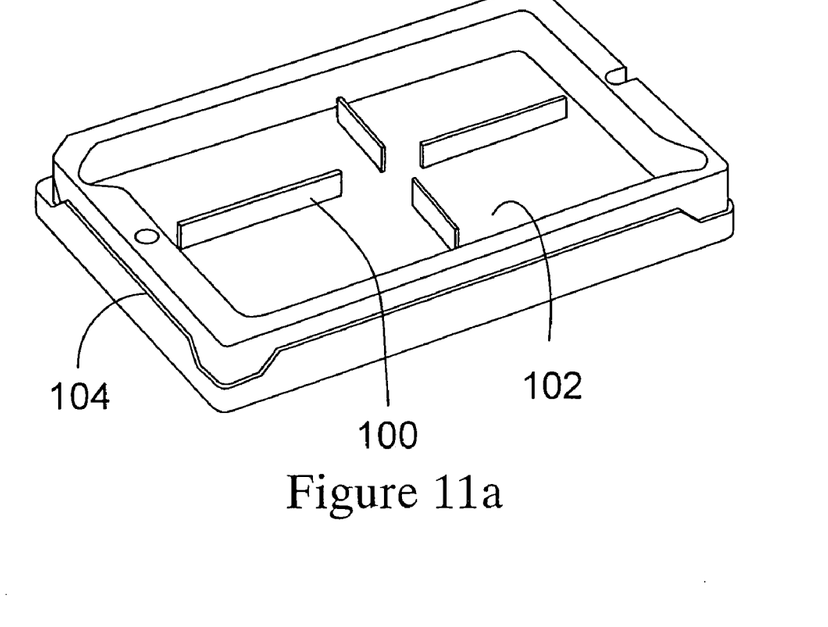
FIGS. 11a–11d are perspective views of alternative embodiments of the single well feeding plate of FIG. 10 of the present invention.
Figure 11B:
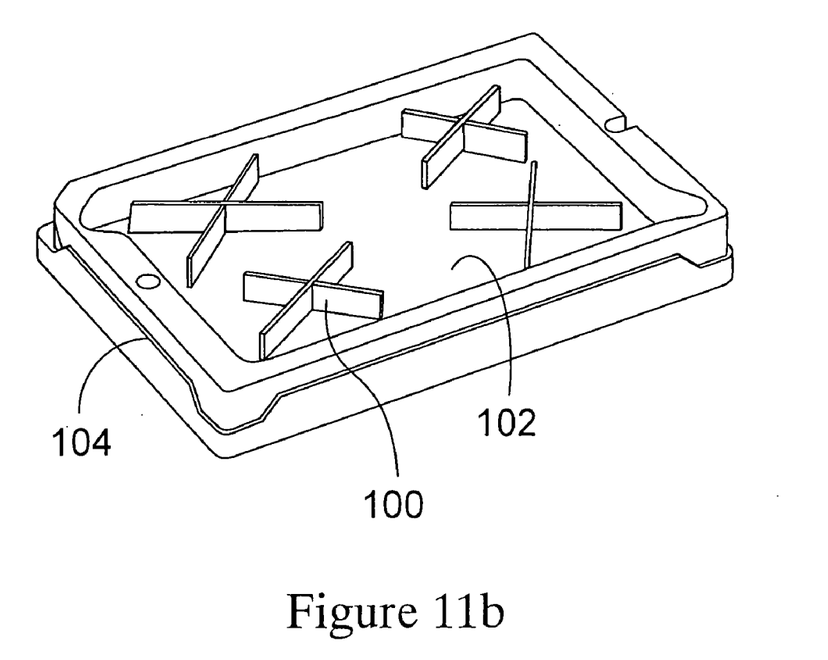
Figure 11C:
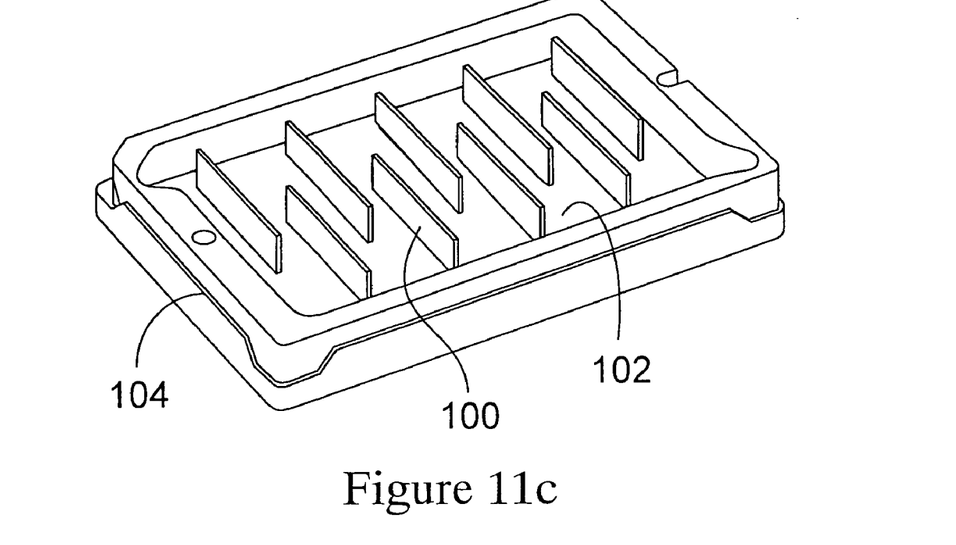
Figure 11D:
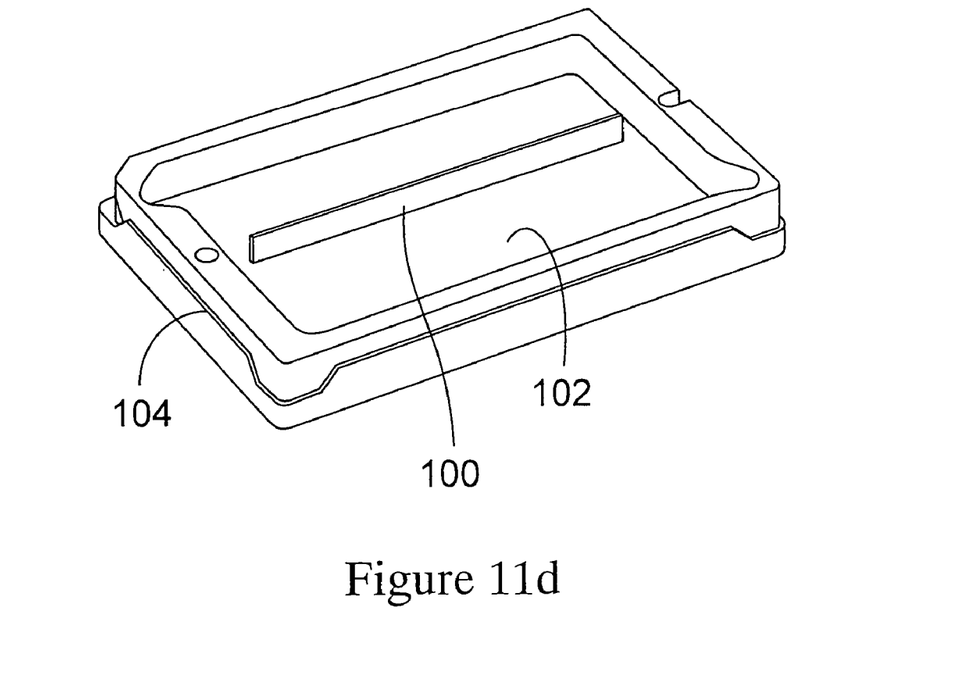

FIG. 11a shows an alternative arrangement of baffles in the embodiment of FIG. 10. In this Figure, straight baffles 100 are used instead of the wavy baffle design of FIG. 10. In FIG. 11b, the use of a series of repetitive baffles 100 is shown. Here, the baffles are shown as a series of "X" patterns spread across the feed tray bottom. FIG. 11c shows the use of a series of baffles 100 arranged in parallel and spaced part relationship to each other and each other baffle 100 extends out from the same sidewall. In FIG. 11d is shown a single baffle that extend substantially the length of the feed tray.

Those baffles 100 may if desired have one or more through holes in them adjacent their bottom surface with the tray so as to allow for unimpeded flow through out the tray. Alternatively, in those baffles that are separately formed, the baffles are made such that they only touch the tray bottom at two or more points so that fluid may flow under the baffle(s).

In another embodiment, the baffle(s) may be used in lieu of the posts or protrusions discussed above as the means for allowing one to remove excess liquid from the bottom of the cell plate during its removal from the feed tray. In this embodiment (not shown), the baffle(s) should be of a height similar to that of the post or protrusions discussed above. Further, the number of baffles used should sufficient to ensure that all wells of the cell plate receive sufficient force so as to knock off any droplets without disturbing the cells growing in the plate.

While the embodiments of the present invention have been shown as being directed to a filter plate with 96 wells other well configurations such as 6.12, 24, 48 or 384 may also be used. In all events, the second receiver plate and the multiwell feeding plate if multiwell, should have he same number of wells as the filter plate an d be in alignment with the wells of the filter plate.

We claim:

1. A multiwell cell growth apparatus comprising a multiwell filter plate and a feeding plate, said multiwell filter plate having a multiplicity of wells extending from the plate, each of said wells comprising (a) a hollow member having two openings and extending from said plate and (b) a permeable barrier secured about said lower opening, said feeding plate having one well to accommodate said multiplicity of wells of the filter plate, and wherein said multiwell filter plate has one or more first access holes for introducing and removing a liquid into and from said feeding plate and further comprising a series of second access holes in the filter plate located adjacent the wells for recovering liquid from said feeding plate.

2. A multiwell cell growth apparatus comprising a multiwell filter plate and a feeding plate, said multiwell filter plate having a multiplicity of wells extending from the plate, each of said wells comprising (a) a hollow member having two openings and extending from said plate and (b) a microporous filter secured about said lower opening, one or more first access holes formed in the filter plate for introducing and removing a liquid into and from said feeding plate, said feeding plate having one well to accommodate said filter plate.

3. A multiwell cell growth apparatus comprising a multiwell filter plate and a feeding plate, said multiwell filter plate having a multiplicity of wells extending from the plate, each of said wells comprising (a) a hollow member having two openings and extending from said plate and (b) a microporous filter secured about said lower opening, one or more first access holes formed in the filter plate for introducing and removing a liquid into and from said feeding plate, a multiplicity of second access holes in the filter plate and arranged to be adjacent to and in the same number as the wells of the filter plate, said feeding plate having one well to accommodate said filter plate.

4. A multiwell cell growth apparatus comprising a multiwell filter plate and a feeding plate, said multiwell filter plate having 96 wells extending from the plate, each of said wells comprising (a) a hollow member having two openings and extending from said plate and (b) a microporous filter secured about said lower opening, one or more first access holes formed in the filter plate for introducing and removing a liquid into and from said feeding plate, 96 second access holes in the filter plate and arranged to be adjacent to the wells of the filter plate, said feeding plate having one well to accommodate said filter plate.

5. A multiwell cell growth apparatus comprising a multiwell filter plate and a feeding plate, said multiwell filter plate having a multiplicity of wells extending from the plate, each of said wells comprising (a) a hollow member having two openings and extending from said plate and (b) a microporous filter secured about said lower opening, one or more first access holes formed in the filter plate for introducing and removing a liquid into and from said feeding plate, a multiplicity of second access holes in the filter plate and arranged to be adjacent to and in the same number as the wells of the filter plate, said feeding plate having one well to accommodate said filter plate.

* * * * *